United States Patent
Sugito et al.

(10) Patent No.: US 6,926,703 B2
(45) Date of Patent: Aug. 9, 2005

(54) DISPOSABLE DIAPER WITH TUBULAR LIQUID-DISTRIBUTING PASSAGE

(75) Inventors: Tomoko Sugito, Kagawa-ken (JP); Yoshitaka Mishima, Kagawa-ken (JP)

(73) Assignee: Uni-Charm Corporation, Shikokuchuo (JP)

( * ) Notice: Subject to any disclaimer, the term of this patent is extended or adjusted under 35 U.S.C. 154(b) by 0 days.

(21) Appl. No.: 10/757,430

(22) Filed: Jan. 15, 2004

(65) Prior Publication Data

US 2004/0147891 A1 Jul. 29, 2004

(30) Foreign Application Priority Data

Jan. 17, 2003 (JP) ........................................ 2003-009351

(51) Int. Cl.⁷ ............................................. A61F 13/15
(52) U.S. Cl. ................................. 604/385.101; 604/378
(58) Field of Search ....................... 604/385.01, 385.19, 604/85.3, 97, 685.01, 685.19, 685.3

(56) References Cited

U.S. PATENT DOCUMENTS

| | | | | |
|---|---|---|---|---|
| 5,762,642 A | * | 6/1998 | Coles et al. | 604/378 |
| 5,846,230 A | * | 12/1998 | Osborn et al. | 604/378 |
| 5,913,851 A | * | 6/1999 | Gryskiewicz et al. | 604/385.31 |
| 6,262,331 B1 | * | 7/2001 | Nakahata et al. | 604/383 |
| 6,316,688 B1 | * | 11/2001 | Hammons et al. | 604/378 |
| 6,383,170 B1 | * | 5/2002 | Mishima et al. | 604/385.19 |
| 6,436,083 B1 | * | 8/2002 | Mishima et al. | 604/385.24 |
| 2004/0087924 A1 | * | 5/2004 | Sroda et al. | 604/367 |

FOREIGN PATENT DOCUMENTS

| | | | | |
|---|---|---|---|---|
| JP | 9-51913 | | 2/1997 | |
| WO | WO 9014063 A1 | * | 11/1990 | A61F/13/46 |

* cited by examiner

*Primary Examiner*—Larry I. Schwartz
*Assistant Examiner*—Laura C. Hill
(74) *Attorney, Agent, or Firm*—Lowe Hauptman & Berner, LLP

(57) ABSTRACT

A disposable diaper includes a liquid absorbent core having upper and lower surfaces and extending over a crotch region and further into front and rear waist regions, a liquid-pervious first sheet having an upper section covering the upper surface of the core and a lower section covering the lower surface of the core, and a liquid-impervious second sheet lying outside the lower section of the first sheet. The core is formed with a slit extending completely through in the thickness direction from the upper surface to the lower surface and extending in the longitudinal direction from the front waist region to the crotch region. The upper and lower sections of the first sheet define a tubular liquid passage extending along a longitudinal center line from the front waist region to the crotch region.

20 Claims, 9 Drawing Sheets

DISPOSABLE DIAPER WITH TUBULAR LIQUID-DISTRIBUTING PASSAGE

BACKGROUND OF THE INVENTION

The present invention relates to disposable diapers for absorption and contaimnent of bodily discharges. The present application is based on, and claims priority from, Japanese Application Serial Number 2003-009351, filed Jan. 17, 2003, the disclosure of which is hereby incorporated by reference herein in its entirety.

There are well known disposable diapers comprising a liquid-pervious topsheet facing the diaper wearer's skin, a liquid-impervious backsheet facing away from the wearer's skin and a liquid-absorbent core interposed between these sheets and configured to define, in a longitudinal direction, a front waist region, a rear waist region and a crotch region extending between these waist regions. This diaper is curved in the longitudinal direction with the topsheet inside, so urine discharged onto the crotch region may smoothly spread from the urine discharged spot in a transverse direction but not in the longitudinal direction. While urine discharged on the diaper put on the wearer is, in principle, absorbed by the core through the topsheet, such absorption is not completed at once but a certain time is taken until a total quantity of discharged urine is absorbed by the core. In order that the core can absorb the total quantity of discharged urine as quickly as possible, a generally entire area of the core is preferably utilized by facilitating discharged urine to spread in the transverse direction as well as in the longitudinal direction.

To meet such requirement, the disposable diaper including a plurality of splits facilitating discharged urine to spread in the transverse direction and at the same time in the longitudinal direction is disclosed, for example, in Japanese Patent Application Publication No. 1997-51913A. These slits are arranged so as to be spaced apart one from another not only in the transverse direction but also in the longitudinal direction and penetrate the core in its thickness direction. Along these splits, the top- and backsheets are put flat and joined together so that the topsheet forms grooves along these splits. With the diaper disclosed in the above-cited Publication, discharged urine is guided into these grooves to spread in the longitudinal direction and at the same time permeates through the core through its area defined between each pair of the grooves which are adjacent in the longitudinal direction to spread in the transverse direction.

In the case of the diaper disclosed in the above-cited Publication, immediately after it has been discharged onto the topsheet, urine spreads on the topsheet and simultaneously flows into the respective grooves. Depending on the particular spot onto which urine has been discharged, there is a possibility that urine might not immediately flow into the grooves and consequently retard urine to spread in the longitudinal direction. If urine is retarded to spread in the longitudinal direction, most of urine will spread in the transverse direction of the diaper and not only make it impossible to utilize the entire area of the core but also cause sideway leakage of urine from the crotch region.

SUMMARY OF THE INVENTION

It is an object of the present invention to provide disposable diapers allowing discharge urine to spread in the longitudinal direction and thereby allowing a generally entire area of the core to be utilized for absorption of urine.

According to the present invention, there is provided a disposable diaper configured to define a front waist region, a rear waist region and a crotch region extending between these waist regions, and comprising a liquid-absorbent core having an upper surface facing a wearer's skin and a lower surface facing away from the wearer's skin and extending over the crotch region and further into the front and rear waist regions, a liquid-pervious first sheet having an upper section covering the upper surface of the core and a lower section covering the lower surface of the core, and a liquid-impervious second sheet lying outside the lower section of the first sheet.

The disposable diaper further comprises the upper section of the first sheet extending upward, in a vicinity of a longitudinal center line bisecting a transverse dimension of the diaper, from the upper surface of the core so as to define a tubular liquid passage extending in the longitudinal direction along the longitudinal center line; and the tubular liquid passage extending at least from the front waist region toward the crotch region.

The present invention includes the following preferred embodiments.

A slit formed completely through the core in its thickness direction along the longitudinal center line extends in the longitudinal direction at least from the front waist region toward the crotch region; and the lower section of the first sheet extends upward from the lower surface of the core through the slit so as to be exposed above the slit, generally describing a loop and cooperates with the upper section to define the tubular liquid passage.

The first sheet is formed from a hydrophilic fibrous nonwoven fabric and the upper section defining the tubular liquid passage has a fiber density higher than a fiber density in a subsection of the upper section except the tubular liquid passage.

The lower section defining the tubular liquid passage has a fiber density higher than a fiber density in a subsection of the lower section except the tubular liquid passage.

DETAILED DESCRIPTION OF THE PREFERRED EMBODIMENTS

Details of a disposable diaper according to the present invention will be more fully understood from the description given hereunder with reference to the accompanying drawings.

Figure 1:
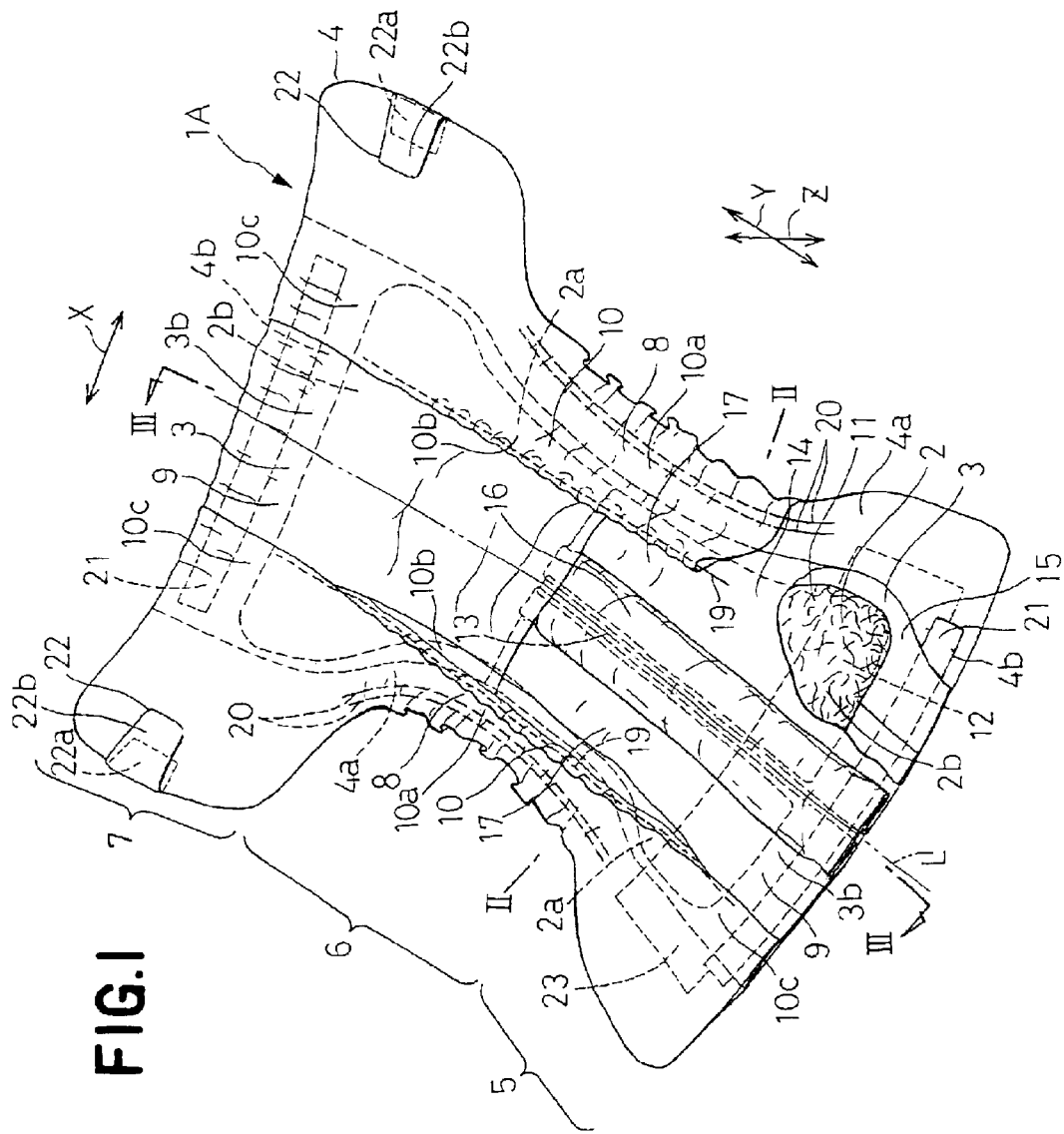
FIG. 1 is a partially cutaway perspective view of a diaper as one embodiment of the invention.
Figure 2:
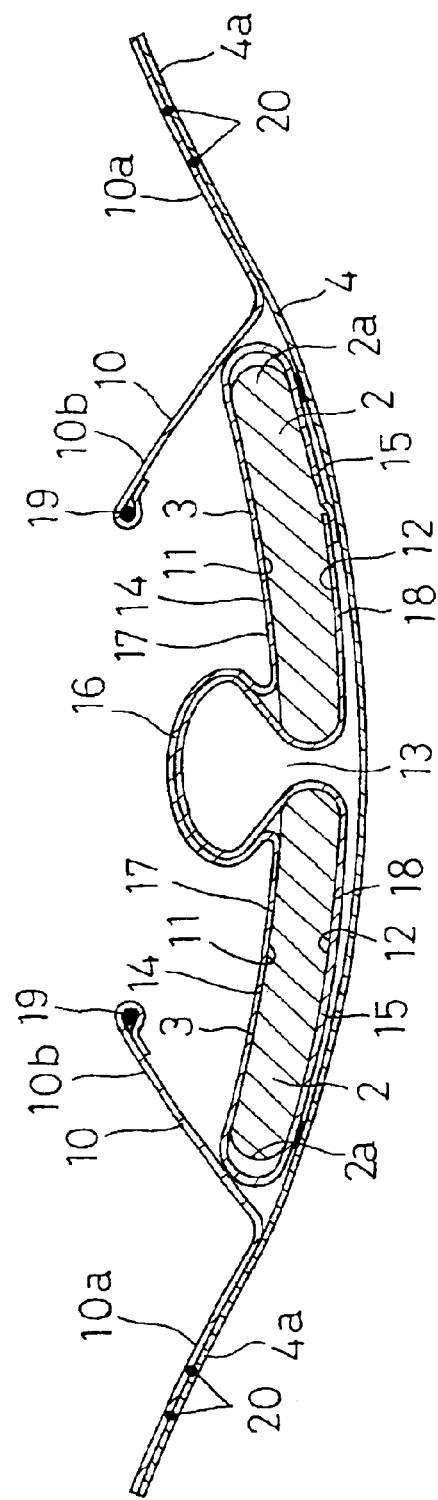
FIG. 2 is a sectional view taken along the line II—II in FIG. 1.
Figure 3:
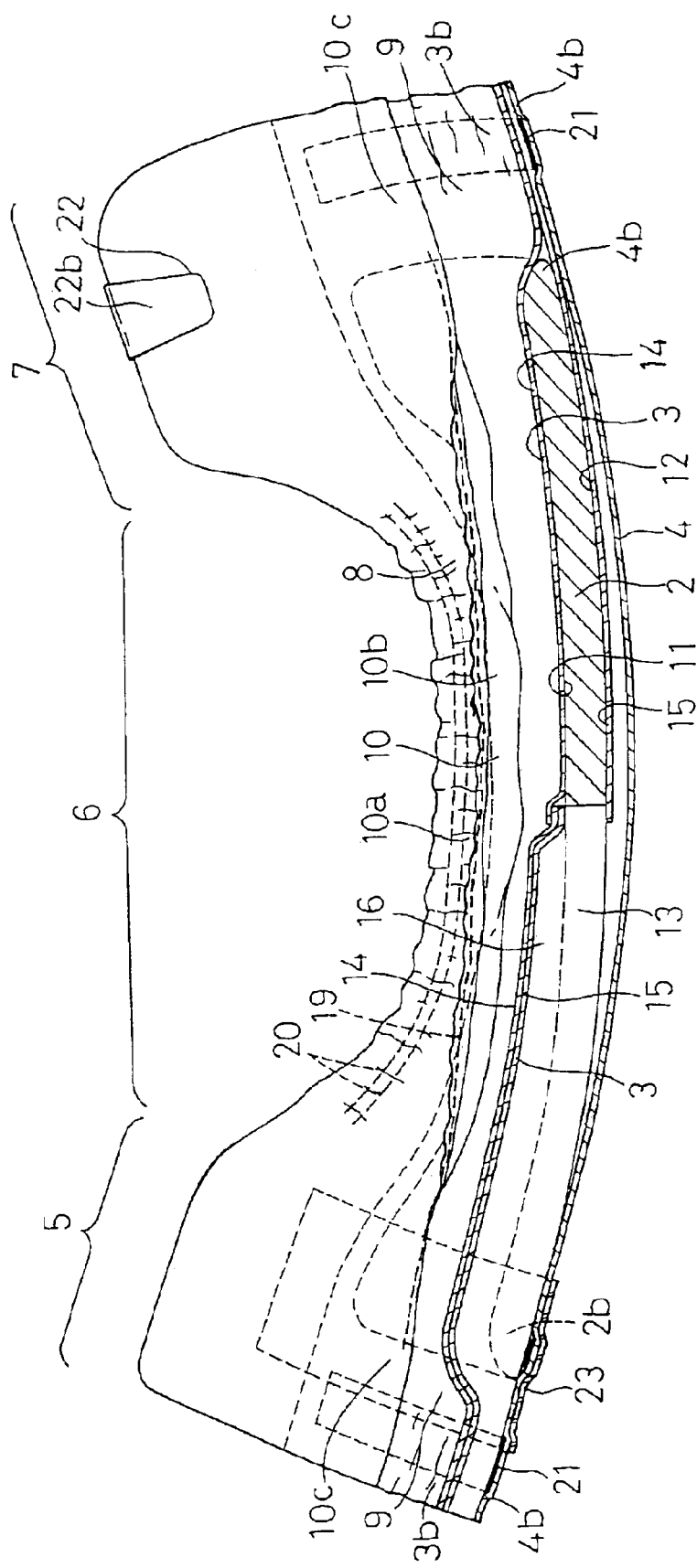
FIG. 3 is a sectional view taken along the line III—III in FIG. 1.

FIG. 1 is a partially cutaway perspective view of a diaper 1A as one embodiment of the invention, FIG. 2 is a sectional view taken along the line II—II in FIG. 1 and FIG. 3 is a sectional view taken along the line III—III in FIG. 1. In FIG. 1, a transverse direction is indicated by an arrow X, a longitudinal direction is indicated by an arrow Y and a thickness direction is indicated by an arrow Z. Term used herein "inner surfaces" of first and second sheets 3, 4 and leak-barrier sheets 10 refers to the surfaces of these sheets 3, 4, 10 facing an absorbent core 2 and term used herein "outer surfaces" of these sheets 3, 4, 10 refers to the surfaces thereof facing away from the core 2.

The diaper 1A comprises the liquid-absorbent core 2, the liquid-pervious first sheet 3 covering the core 2 and a liquid-impervious second sheet 4 lying outside a lower section of the first sheet 3 wherein the lower section will be described later. The diaper 1A is configured to define, in the longitudinal direction, a front waist region 5, a rear waist region 7 and a crotch region 6 extending between these waist regions 5, 7. This diaper 1A is of a so-called open type in which the front and rear waist regions 5, 7 are connected with each other just before the diaper 1A is put on the wearer.

The diaper 1A further comprises a pair of side flaps 8 lying outside transversely opposite side edges 2a of the core 2 and extending in the longitudinal direction between the front and rear waist regions 5, 7 and a pair of end flaps 9 lying outside longitudinally opposite ends 2b of the core 2 and extending in the transverse direction across the front and rear waist regions 5, 7, respectively. In the crotch region 6, the side flaps 8 respectively describe circular arcs which are convex inwardly as viewed in the transverse direction of the diaper 1A. The diaper 1A thus has a generally hourglass-like planar shape. A pair of liquid-impervious leak-barrier sheets 10 extending in the longitudinal direction are attached to the respective side flaps 8.

The core 2 extends over the crotch region 6 and further into the front and rear waist regions 5, 7 and has an upper surface 11 facing the wearer's skin and a lower surface 12 facing away from the wearer's skin. The core 2 has a slit 13 completely through in the thickness direction from the upper surface 11 to the lower surface 12 and extending in the longitudinal direction. More specifically, the slit 13 is formed in the vicinity of a longitudinal center line L bisecting a transverse dimension of the diaper 1A and extends in the front waist region 5 and generally a front half of the crotch region 6. In other words, the slit 13 is formed in a transverse middle of the core 2 and extends generally over a front half thereof.

The core 2 comprises a mixture of fluff pulp and super-absorbent polymer particles or a mixture of fluff pulp, super-absorbent polymer particles and thermoplastic synthetic resin fibers, in any case, compressed to a desired thickness. Preferably, the core 2 is entirely wrapped with a liquid-pervious sheet such as a tissue paper in order to prevent the core 2 from getting out of its initial shape and to prevent the polymer particles from falling off.

The first sheet 3 is formed from a hydrophilic fibrous nonwoven fabric and has an upper section 14 entirely covering the upper surface 11 of the core 2 and a lower section 15 entirely covering the lower surface 12 of the core 2. In the vicinity of the longitudinal center line L (i.e., in the vicinity of the split 13), generally a front half of the upper section 14 extends upward, generally describing a loop. Generally a front half of the lower section 15 extends upwardly from the lower surface of the core 2 beyond the slit 13 and extends upwardly from the upper surface of the core 2, generally describing a loop. The upper and lower sections 14, 15 of the first sheet 3 swell up in this manner to define a tubular liquid passage 16 extending along the longitudinal center line L. The tubular liquid passage 16 has a generally Ω-like cross-section and extends from the front waist region 5 toward the crotch region 6 (See FIGS. 2 and 3).

The subsection 17 of the upper section 14 except the tubular liquid passage 16 has its inner surface intermittently joined to the upper surface 11 of the core 2. The subsection 18 of the lower section 15 has its inner surface intermittently joined to the lower surface 12 of the core 2. The subsection 18 of the lower section 15 has its inner surface intermittently joined to the inner surface of the second sheet 4 along the transversely opposite side edges 2a and the longitudinally opposite ends 2b of the core 2. The upper and lower sections 14, 15 placed upon each other around the tubular liquid passage 16 may be bonded together or not.

A fiber density of the upper section 14 defining the tubular liquid passage 16 is higher than that in the subsection 17 of the upper section 14 except the tubular liquid passage 16. Similarly, a fiber density of the lower section defining the tubular liquid passage 16 is higher than that in the subsection 18 of the lower section 15 except the tubular liquid passage 16. Around the tubular liquid passage 16, the upper and lower sections 14, 15 preferably have a fiber density in a range of $0.5 \times 10^{-5}$ to $18 \times 10^{-5}$ g/mm$^3$ and a basis weight in a range of 10 to 100 g/m$^2$. In the subsections 17, 18, the upper and lower sections 14, 15 preferably have a fiber density in a range of $0.3 \times 10^{-5}$ to $15 \times 10^{-5}$ g/mm$^3$ and a basis weight in a range of 8 to 100 g/m$^2$.

The leak-barrier sheets 10 extend between the longitudinally opposite end flaps 9. The leak-barrier sheets 10 respectively have fixed lateral zones 10a extending in the longitudinal direction outside the side edges 2a of the core 2, movable zones 10b extending in the longitudinal direction and normally biased to rise up above the upper section 14 of the first sheet 3 and longitudinally opposite fixed end zones 10c lying in the front and rear waist regions 5, 7 and collapsed inwardly as viewed in the transverse direction of the diaper 1A. Elastically stretchable members 19 extending in the longitudinal direction are contractibly attached to upper margins of the respective movable zones 10b. These elastic members 19 are secured to the respective movable zones 10b in a manner that these elastic members 19 are wrapped with parts of the respective movable zones 10b.

The side flaps 8 are formed from transversely opposite lateral zones 4a of the second sheet 4 extending outwardly beyond the side edges 2a of the core 2 and the fixed lateral zones 10a of the respective leak-barrier sheets 10. In the respective side flaps 8, the lateral zones 4a of the second sheet 4 and the fixed lateral zones 10a of the respective leak-barrier sheets 10 are put flat together and, along the lateral zones 4a and the fixed lateral zones 10a, these sheets 4, 10 have their inner surfaces joined to each other. A plurality of leg elastic members 20 extending in the longitudinal direction are contractibly attached to the respective side flaps 8. These leg elastic members 20 are interposed between the lateral zones 4a of the second sheet 4 and the fixed lateral zones 10a of the respective leak-barrier sheets 10 and joined to the inner surfaces of these sheets 4, 10.

The end flaps 9 are formed from longitudinally opposite end zones 3b of the first sheet 3 and longitudinally opposite end zones 4b of the second sheet 4 extending outwardly beyond the longitudinally opposite ends of the core 2. In the respective end flaps 9, the end zones 3b of the first sheet 3 and the end zones 4b of the second sheet 3 are put flat together and, along these end zones 3b, 4b, the first and second sheets 3, 4 have their inner surfaces joined to each other. In the respective end flaps 9, the upper and lower sections 14, 15 of the first sheet 3 forming the tubular liquid passage 16 are joined, in a folded up state, to the outer surface of the second sheet 4 at the respective end zones 4b thereof. The longitudinally opposite fixed end zones 10c of the respective leak-barrier sheets 10 are joined to the outer surface of the first sheet 3 at the end zones 3b thereof. Belt-like waist elastic members 21 extending in the transverse direction are contractibly attached to the respective end flaps 10. The waist elastic members 21 are interposed between the end zones 3b of the first sheet 3 and the end zones 4b of the second sheet 4, respectively, and secured to the inner surfaces of these sheets 3, 4.

In the rear waist region 7, the side flaps 8 are provided with flexible tape fasteners 22 made of a plastic film. Each of the tape fasteners 22 has a fixed end zone 22a and a free end zone 22b both extending in the transverse direction. The fixed end zone 22a is interposed between the associated lateral zone 4a of the second sheet 4 and the fixed lateral zone 10a of the associated leak-barrier sheet 10 and joined to the inner surfaces thereof. The inner surface of the free end zone 22b is coated with a pressure-sensitive adhesive (not shown). The free end zone 22b is folded inwardly as viewed in the transverse direction and releasably bonded to the lateral zone 10a of the associated leak-barrier sheet 10 by means of a pressure-sensitive adhesive. The front waist region 5 is provided with a flexible target tape strip 23 attached thereto, on which the free end zones 22b of the respective tape fasteners 22 are detachably anchored. The target tape strip 23 is made of a plastic film and shaped in a rectangle of which long sides extend in the transverse direction. The target tape strip 23 is joined to the outer surface of the second sheet 4.

To put the diaper 1A on the wearer, the side flaps 8 in the rear waist region 7 are placed upon the outer surfaces of the side flaps 8 in the front waist region 5 and then the free end zones 22b of the respective tape fasteners 22 are anchored on the target tape strip 23 to connect the front waist region 5 and the rear waist region 7 with each other. Thereupon, the diaper 1A is formed by a waist-hole and a pair of leg-holes below the waist-hole (not shown).

The tubular liquid passage 16 is placed against the wearer's urethral region as the diaper 1A is put on the wearer. Urine discharged on the diaper 1A permeates through the tubular liquid passage 16 first so as to spread in the longitudinal direction under a capillary effect of this passage 16, then vertically permeates downward through the tubular liquid passage 16 so as to spread in the transverse direction through the subsection 17 of the upper section 14 except the tubular liquid passage 16 as well as through the subsection 18 of the lower section 15 except the tubular liquid passage 16. Finally, urine is absorbed through the upper section 14 and then the upper surface 11 of the core 2 into the core 2, on one hand, and through the lower section 15 and then the lower surface of the core 2 into the core 2, on the other hand.

The tubular liquid passage 16 has a fiber density higher than those in the subsections 17, 18 of the upper and lower sections 14, 15 except the tubular liquid passage 16 and this is for the reason that the capillary phenomenon occurring in the tubular liquid passage 16 allowing urine to spread in the longitudinal direction before urine can move from the tubular liquid passage 16 to the subsections 17, 18. Even after urine has moved from the tubular liquid passage 16 to the subsections 17, 18, spread of urine in the longitudinal direction is sufficiently promoted relative to spread of urine in the transverse direction to ensure that spread of urine in the longitudinal direction can progress before urine spreads in the transverse direction.

Immediately after quick spread in the longitudinal direction under the capillary phenomenon of the tubular liquid passage, urine spread also in the transverse direction through the subsections 17, 18 of the upper and lower sections 14, 15. In this way, a generally entire area of the core 2 can be utilized to absorb urine and a total quantity of urine discharged on the diaper 1A can be absorbed into the core in a time as short as possible. In the case of this diaper 1A, sideway leakage of urine can be reliably prevented since there is no possibility that urine might immediately spread from the spot onto which urine has been discharged in the transverse direction.

If the fiber density of the upper and lower section 14, 15 around the tubular liquid passage 16 is less than $0.5 \times 10^{-5}$ g/mm$^3$, the capillary phenomenon occurring along the tubular liquid passage 16 will be too weak to promote spread of urine along the tubular liquid passage 16 in the longitudinal direction and will cause a premature spread of urine in the transverse direction. This will lead to sideway leakage of urine. If the fiber density of the subsections 17, 18 of the upper and lower sections 14, 15 except the tubular liquid passage 16 is less than $0.3 \times 10^{-5}$ g/mm$^3$, the capillary phenomenon occurring in these subsections 17, 18 will be too weak for urine to spread in the transverse direction through these subsections 17, 18 and a certain quantity of urine may stay along the bottom of the tubular liquid passage 16.

The movable zones 10b of the respective leak-barrier sheets 10 rise up above the upper section 14 under a contractile force of the elastic members 19 as the diaper 1A is curved in the longitudinal direction with the upper section 14 of the first sheet 3 inside. These rising movable zones 10b of the respective leak-barrier sheets 10 form barriers against urine and reliably prevent sideway leakage of urine which would otherwise occur beyond the side flaps 8.

Figure 4:
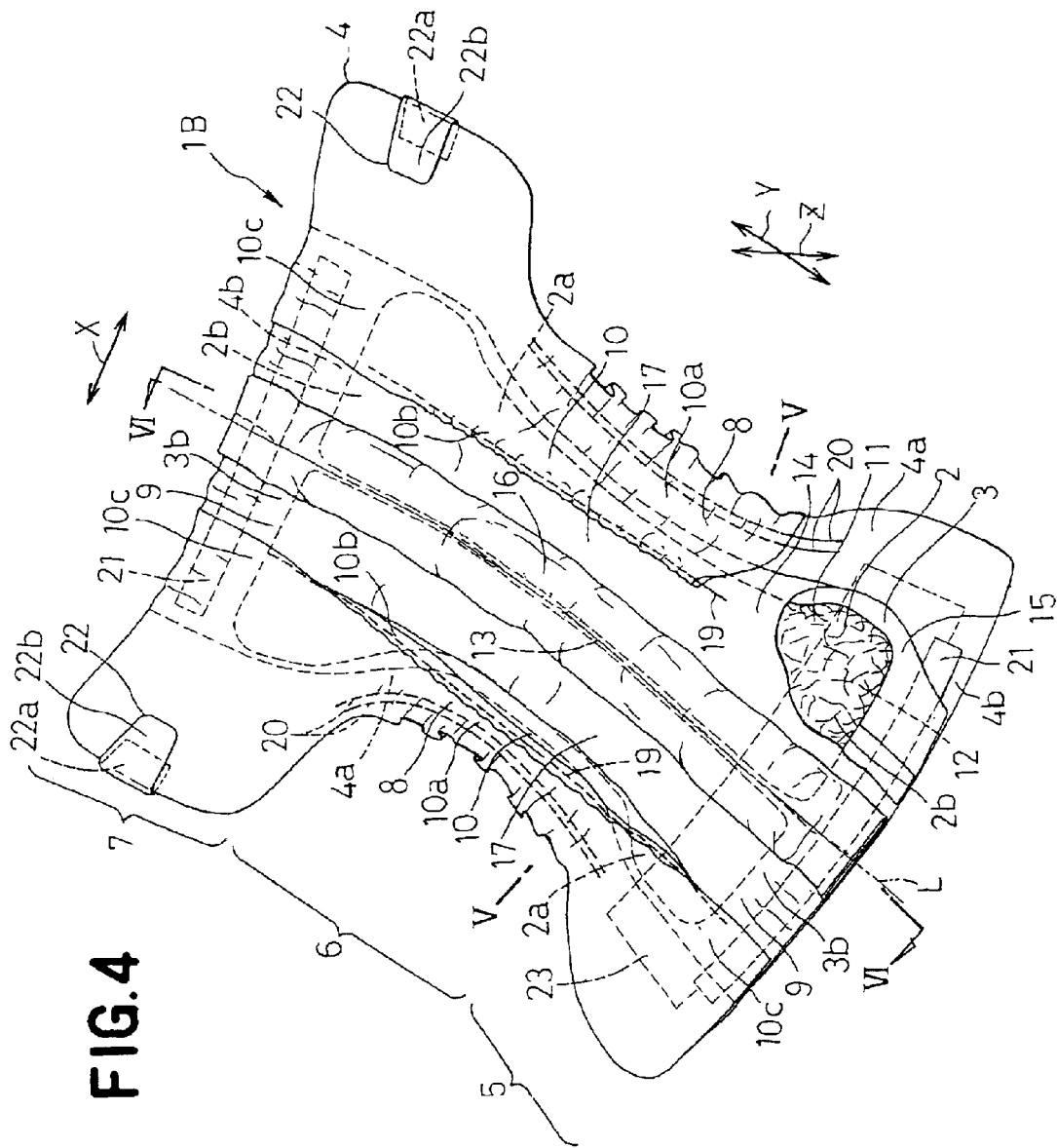
FIG. 4 is a partially cutaway perspective view showing one preferred embodiment of the invention.
Figure 5:
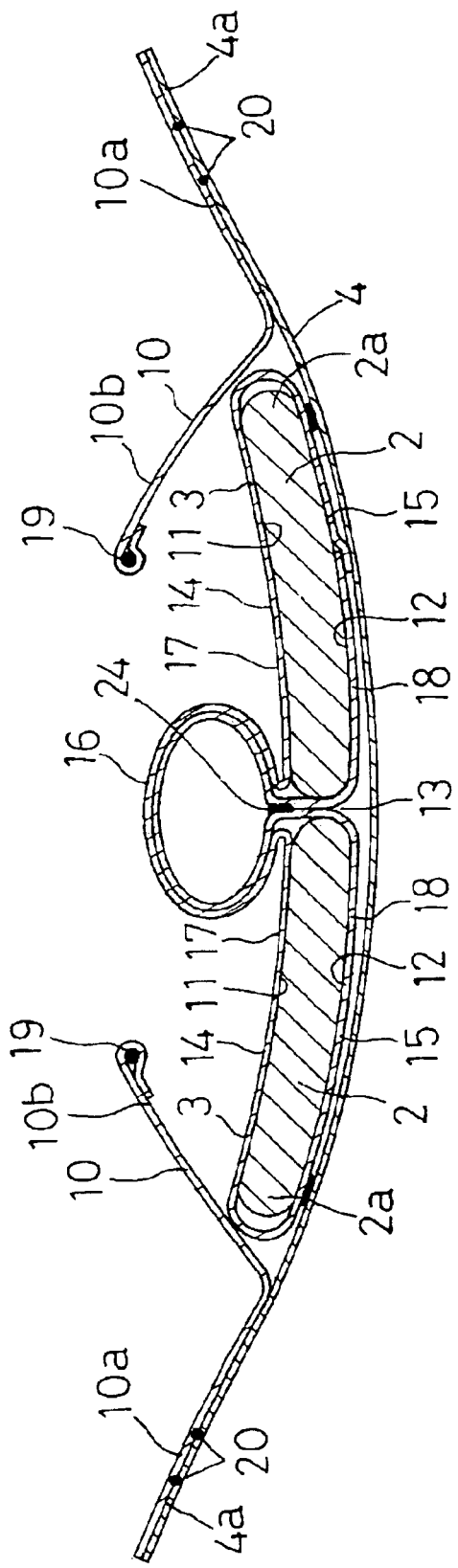
FIG. 5 is a sectional view taken along the line V—V in FIG. 4.
Figure 6:
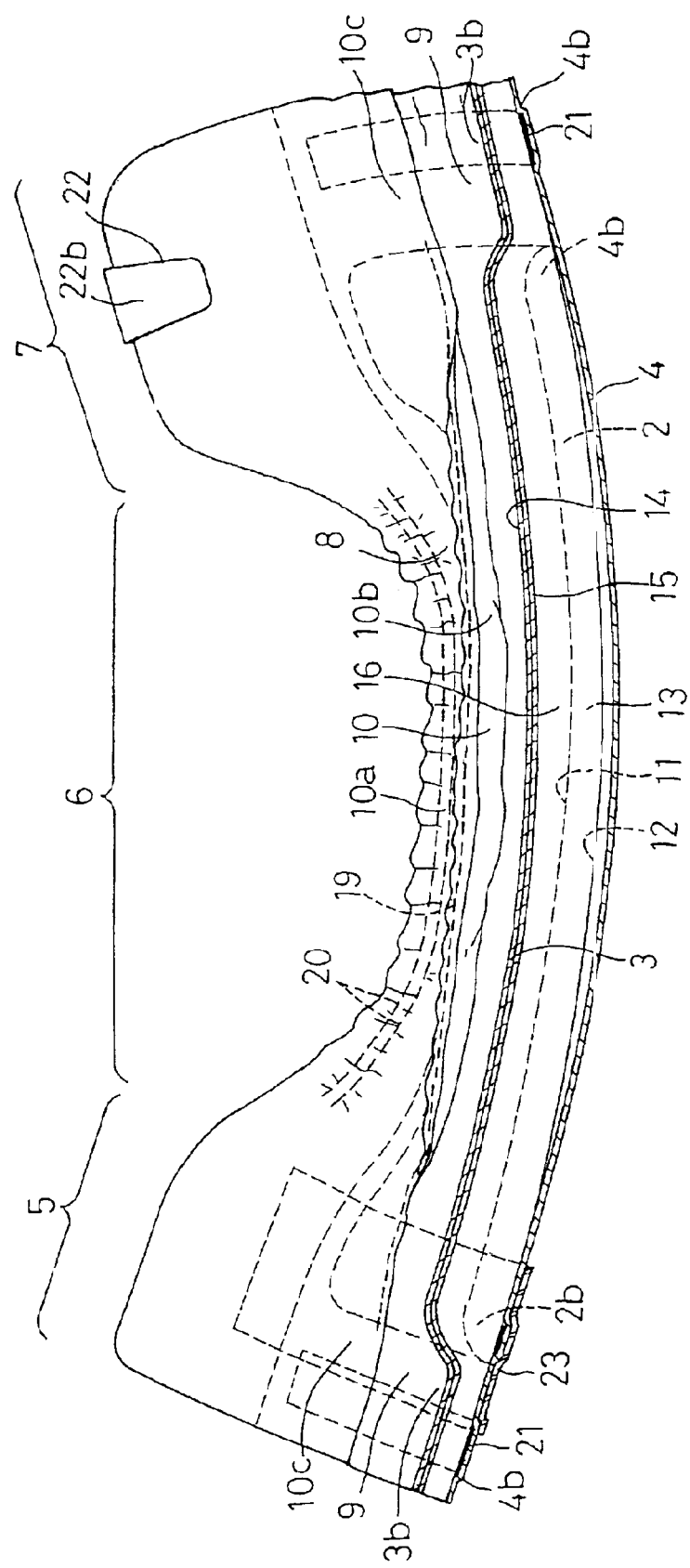
FIG. 6 is a sectional view taken along the line VI—VI in FIG. 4.

FIG. 4 is a partially cutaway perspective view of a diaper 1B as one preferred embodiment of the invention, FIG. 5 is a sectional view taken along the line V—V in FIG. 4 and FIG. 6 is a sectional view taken along the line VI—VI in FIG. 4. In FIG. 4, a transverse direction is indicated by an arrow X, a longitudinal direction is indicated by an arrow Y and a thickness direction is indicated by an arrow Z.

The diaper 1B comprises the liquid-absorbent core 2, the liquid-pervious first sheet 3 and a liquid-impervious second sheet 4. The diaper 1B is configured to define, in the longitudinal direction, a front waist region 5, a rear waist region 7 and a crotch region 6 extending between these waist regions 5, 7. This diaper 1B further includes a pair of side flaps 8 extending in the longitudinal direction and a pair of end flaps 9 extending in the transverse direction. The side flaps 8 are respectively provided with a pair of liquid-impervious leak-barrier sheets 10 extending in the longitudinal direction.

The core 2 extends over the crotch region 6 and further into the front and rear waist regions 5, 7 in the same manner as in the case illustrated by FIG. 1. The core 2 has an upper surface 11 facing the wearer's skin and a lower surface 12 facing away from the wearer's skin. The core 2 has a slit 13 completely through in the thickness direction from the upper surface 11 to the lower surface 12 and extending in the longitudinal direction. More specifically, the slit 13 is formed in the vicinity of a longitudinal center line L bisecting a transverse dimension of the diaper 1B and extends between the front and rear waist region 5, 7. In other words, the slit 13 is formed in a transverse middle of the core 2 and extends substantially over a full length of the core 2 in the longitudinal direction.

The first sheet 3 is formed from a hydrophilic fibrous nonwoven fabric and has an upper section 14 entirely covering the upper surface 11 of the core 2 and a lower section 15 entirely covering the lower surface 12 of the core 2. In the vicinity of the longitudinal center line L (i.e., in the vicinity of the split 13), the upper section 14 extends upwardly, generally describing a loop. The lower section 15 extends upwardly from the lower surface 12 of the core 2 beyond the slit 13 and extends upwardly from the upper surface of the core 2, generally describing a loop. The upper and lower sections 14, 15 swell up in this manner to define a tubular liquid passage 16 extending along the longitudinal center line L. The tubular liquid passage 16 has a generally Ω-like cross-section and extends from the front waist region 5 toward the crotch region 6 (See FIGS. 2 and 3).

The tubular liquid passage 16 has a generally Ω-like cross-section and extends from the front waist region 5 toward the crotch region 6 (See FIGS. 5 and 6). Immediately below the tubular liquid passage 16, the upper and lower sections 14, 15 of the first sheet 3 are put flat and joined together by means of adhesive spots 24 arranged intermittently in the longitudinal direction.

The subsection 17 of the upper section 14 except the tubular liquid passage 16 has its inner surface intermittently joined to the upper surface 11 of the core 2. The subsection 18 of the lower section 15 has its inner surface intermittently joined to the lower surface 12 of the core 2. The subsection 18 of the lower section 15 has its inner surface intermittently joined to the inner surface of the second sheet 4. The upper and lower sections 14, 15 placed upon each other around the tubular liquid passage 16 may be joined together or not.

A fiber density of the upper section 14 defining the tubular liquid passage 16 is higher than that in the subsection 17 of the upper section 14 except the tubular liquid passage 16. Similarly, a fiber density of the lower section defining the tubular liquid passage 16 is higher than that in the subsection 18 of the lower section 15 except the tubular liquid passage 16. Around the tubular liquid passage 16, the upper and lower sections 14, 15 preferably have a fiber density and a basis weight as has previously been specified in the connection with FIG. 1 and in the subsections 17, 18 also, the upper and lower sections 14, 15 preferably have a fiber density and a basis weight as has previously been specified in the connection with FIG. 1.

The leak-barrier sheets 10 respectively have fixed lateral zones 10a extending in the longitudinal direction, movable zones 10b extending in the longitudinal direction and normally biased to rise on the upper section 14 of the first sheet 3 and longitudinally opposite fixed end zones 10c lying in the front and rear waist regions 5, 7 and collapsed inward as viewed in the transverse direction of the diaper 1B. Elastic members 19 extending in the longitudinal direction are contractibly attached to upper margins of the respective movable zones 10b.

The side flaps 8 are formed from transversely opposite lateral zones 4a of the second sheet 4 and the fixed lateral zones 10a of the respective leak-barrier sheets 10. A plurality of leg elastic members 20 extending in the longitudinal direction are contractibly attached to the respective side flaps 8. The end flaps 9 are formed from longitudinally opposite end zones 3b of the first sheet 3 and longitudinally opposite end zones 4b of the second sheet 4. In the respective end flaps 9, the end zones 3b of the first sheet 3 and the end zones 4b of the second sheet 3 are put flat together and joined in such state to the second sheet 4. The longitudinally opposite fixed end zones 10c of the respective leak-barrier sheets 10 are joined to the end zones 3b of the first sheet 3. Belt-like waist elastic members 21 extending in the transverse direction are contractibly attached to the respective end flaps 10.

In the rear waist region 7, the side flaps 8 are provided with flexible tape fasteners 22 of which respective free end zones 22b are coated with a pressure-sensitive adhesive (not shown). The front waist region 5 is provided with a flexible target tape strip 23 attached thereto, on which the free end zones 22b of the respective tape fasteners 22 are detachably anchored.

Urine discharged on the diaper 1B on the wearer permeates through the tubular liquid passage 16 first so as to spread in the longitudinal direction under a capillary phenomenon occurring in this passage 16, then vertically permeates downward through the tubular liquid passage 16 so as to spread in the transverse direction through the subsections 17, 18 of the upper and lower sections 14, 15. The tubular liquid passage 16 extends into the rear waist region 7 and allows urine to spread toward the rear waist region-7 so that the area of the core 2 lying in the rear waist region 7 can be efficiently utilized to absorb urine. Finally, urine is absorbed through the upper section 14 and then the upper surface 11 of the core 2 into the core 2, on one hand, and through the lower section 15 and then the lower surface of the core 2 into the core 2, on the other hand.

The tubular liquid passage 16 has a fiber density higher than those in the subsections 17, 18 of the upper and lower sections 14, 15 and this is for the reason that the capillary phenomenon occurring in the tubular liquid passage 16 allowing urine to spread in the longitudinal direction before urine can move from the tubular liquid passage 16 to the subsections 17, 18.

Immediately after quick spread in the longitudinal direction under the capillary phenomenon of the tubular liquid passage, urine spread also in the transverse direction through the subsections 17, 18 of the upper and lower sections 14, 15. In this way, a generally entire area of the core 2 can be utilized to absorb urine and a total quantity of urine discharged on the diaper 1B can be absorbed into the core in a time as short as possible. In the case of this diaper 1B, sideway leakage of urine can be reliably prevented since there is no possibility that urine might immediately spread from the spot onto which urine has been discharged in the transverse direction. In this diaper 1B also, the movable zones 10b of the respective leak-barrier sheets 10 rise and form barriers against urine to prevent any quantity of urine from leaking sideways beyond the side flaps 8.

Figure 7:
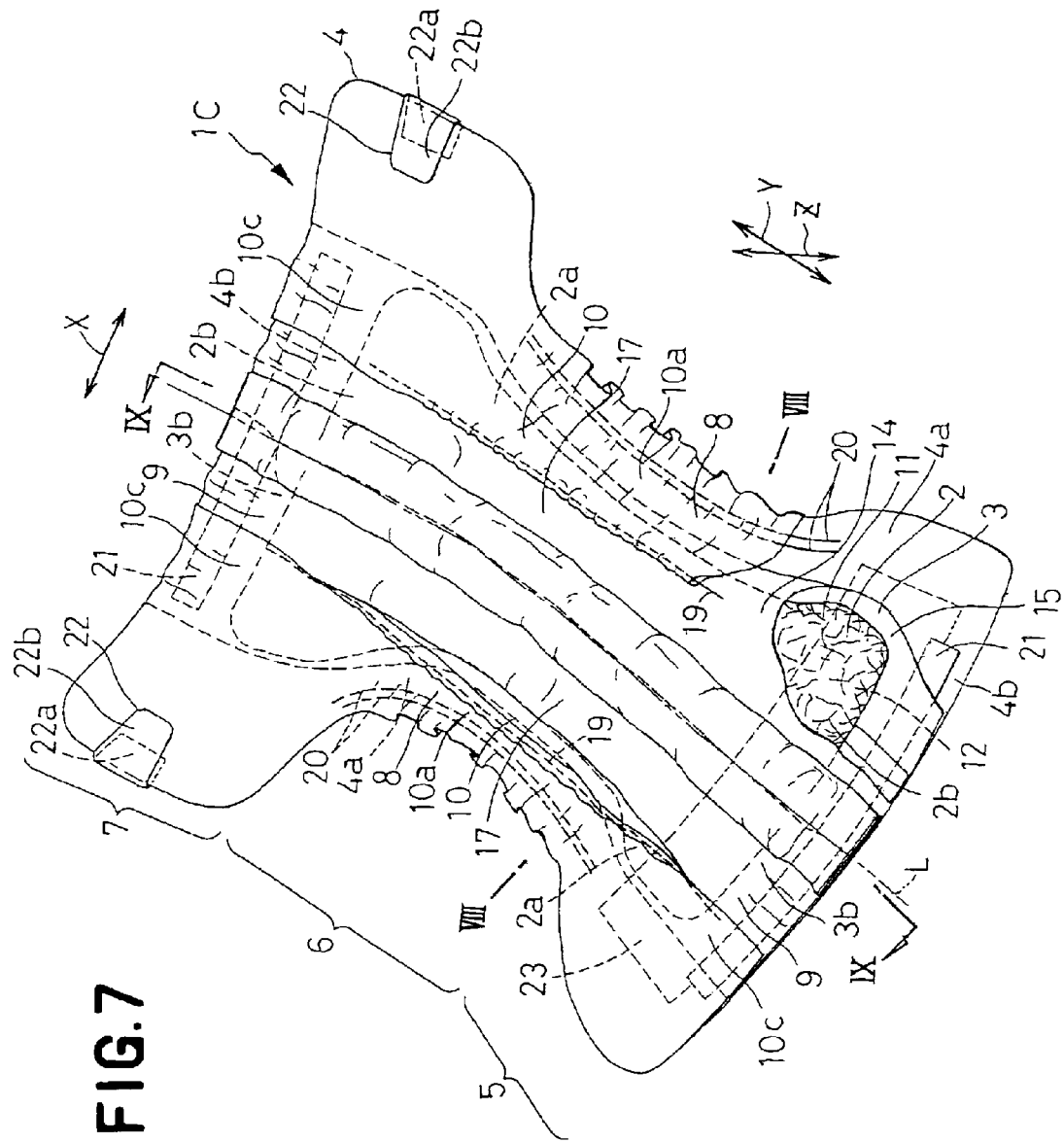
FIG. 7 is a partially cutaway perspective view showing another preferred embodiment of the invention.
Figure 8:
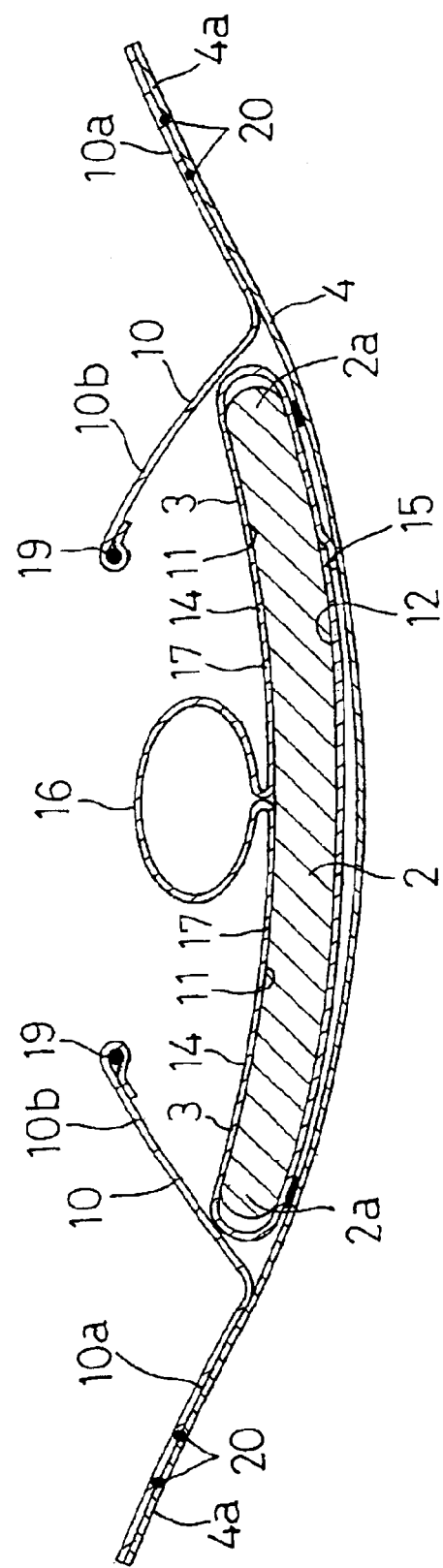
FIG. 8 is a sectional view taken along the line VIII—VIII in FIG. 7.
Figure 9:
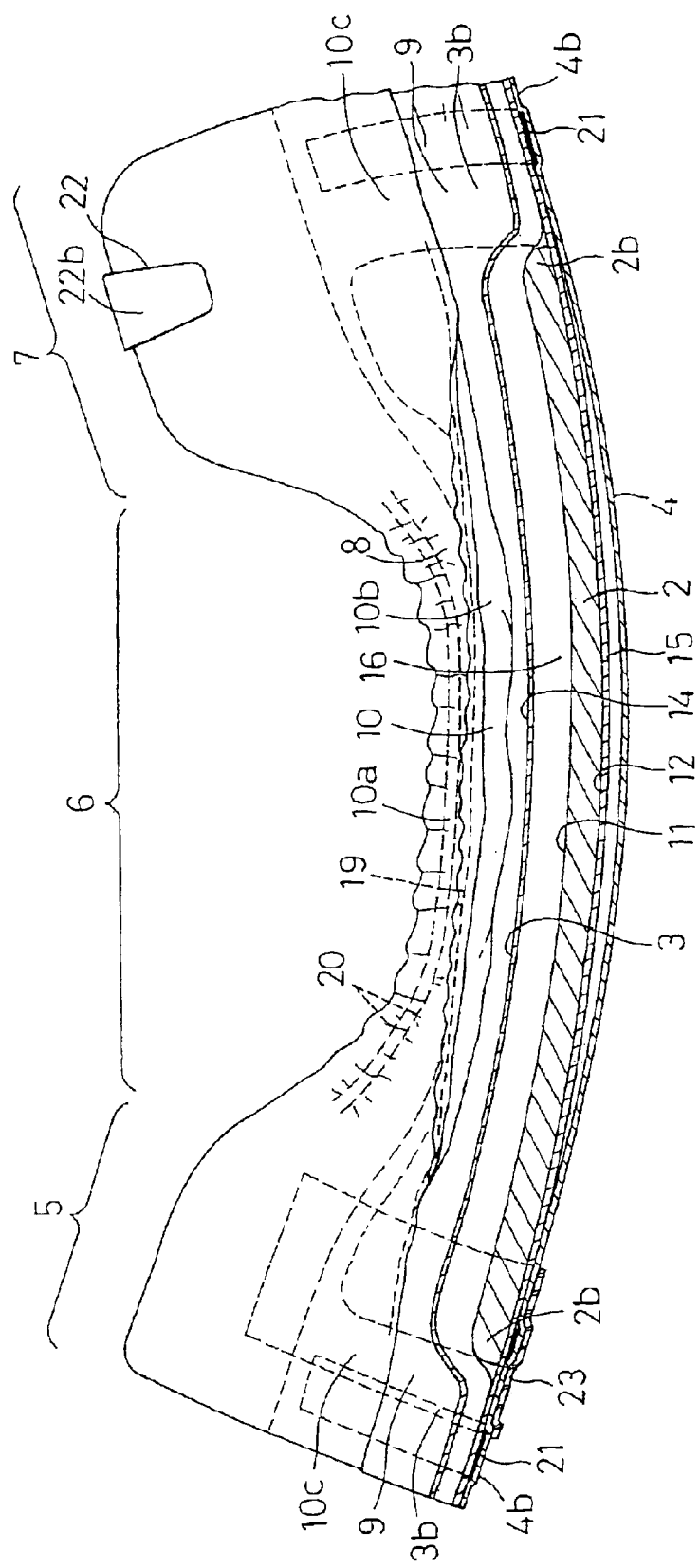
FIG. 9 is a sectional view taken along the line IX—IX in FIG. 7.

FIG. 7 is a partially cutaway perspective view showing a diaper 1C as another preferred embodiment of the invention, FIG. 8 is a sectional view taken along the line VIII—VIII in FIG. 7 and FIG. 9 is a sectional view taken along the line IX—IX in FIG. 7. In FIG. 7, a transverse direction is indicated by an arrow X, a longitudinal direction is indicated by an arrow Y and a thickness direction is indicated by an arrow Z.

The diaper 1C comprises the liquid-absorbent core 2, the liquid-pervious first sheet 3 and a liquid-impervious second sheet 4. The diaper 1C is configured to define, in the longitudinal direction, a front waist region 5, a rear waist region 7 and a crotch region 6 extending between these waist regions 5, 7. This diaper 1C further includes a pair of side flaps 8 extending in the longitudinal direction and a pair of end flaps 9 extending in the transverse direction. The side flaps 8 are respectively provided with liquid-impervious leak-barrier sheets 10 extending in the longitudinal direction. The core 2 is identical to that in the case illustrated by FIG. 1 and extending over the crotch region 6 and further into the front and rear waist regions 5, 7. The core 2 has an upper surface 11 facing the wearer's skin and a lower surface 12 facing away from the wearer's skin.

The first sheet 3 is formed from a hydrophilic fibrous nonwoven fabric and has an upper section 14 entirely covering the upper surface 11 of the core 2 and a lower section 15 entirely covering the lower surface 12 of the core 2. In the vicinity of the longitudinal center line L, the upper section 14 extends upward from the upper surface 11 of the core 2, generally describing a loop. The upper section 14 extends upward in this manner to define a tubular liquid passage 16 extending along the longitudinal center line L. The tubular liquid passage 16 presents a generally Ω-like cross-section and extends from the front waist region 5 toward the rear waist region 7 (See FIGS. 8 and 9). The subsection 17 of the upper section 14 except the tubular liquid passage 16 has its inner surface intermittently joined to the upper surface 11 of the core 2 and the subsection 18 of the lower section 15 has its outer surface intermittently joined to the inner surface of the second sheet 4.

A fiber density of the upper section 14 defining the tubular liquid passage 16 is higher than that in the subsection 17 of the upper section 14 except the tubular liquid passage 16. The fiber density and the basis weight of the upper section 14 defining the tubular liquid passage 16 are preferably in the same ranges as have previously been specified in the connection with FIG. 1 and the fiber density and the basis weight of the subsection 17 of the upper section 14 are also in the same ranges as have previously been specified in the connection with FIG. 1.

The leak-barrier sheets 10 respectively have fixed lateral zones 10a extending in the longitudinal direction, movable zones 10b normally biased to rise on the upper section 14 and longitudinally opposite fixed end zones 10c lying in the front and rear waist regions 5, 7 and collapsed inward as viewed in the transverse direction of the diaper 1C. Stretchable elastic members 19 extending in the longitudinal direction are contractibly attached to upper margins of the respective movable zones 10b.

The side flaps 8 are formed from transversely opposite lateral zones 4a of the second sheet 4 and the fixed lateral zones 10a of the respective leak-barrier sheets 10. A plurality of leg elastic members 20 extending in the longitudinal direction are contractibly attached to the respective side flaps 8. The end flaps 9 are formed from the end zones 3b of the first sheet 3 and the end zones 4b of the second sheet 4. In the respective end flaps 9, the upper section 14 of the first sheet 3 defining the tubular liquid passage 16 is folded up and bonded to the second sheet 4 in such a folded up state. The longitudinally opposite fixed end zones 10c of the respective leak-barrier sheets 10 are joined to the end zones 3b of the first sheet 3. Belt-like waist elastic members 21 extending in the transverse direction are contractibly attached to the respective end flaps 9.

In the rear waist region 7, the side flaps 8 are provided with flexible tape fasteners 22 of which respective free end zones 22b are coated with a pressure-sensitive adhesive (not shown). The front waist region 5 is provided with a flexible target tape strip 23 attached thereto, on which the free end zones 22b of the respective tape fasteners 22 are detachably anchored. The target tape strip 23 is shaped in a rectangle of which long sides extend in the transverse direction.

Urine discharged on the diaper 1C on the wearer permeates through the tubular liquid passage 16 first so as to spread in the longitudinal direction under a capillary phenomenon occurring in this passage 16, then vertically permeates downward through the tubular liquid passage 16 so as to spread in the transverse direction through the subsection 17 of the upper section 14. The tubular liquid passage 16 extends into the rear waist region 7 and allows urine to spread toward the rear waist region 7. Therefore, the area of the core 2 lying in the rear waist region 7 can be efficiently utilized to absorb urine. Finally, urine is absorbed through the upper section 14 and then the upper surface 11 of the core 2 into the core 2. In the diaper 1C also, the fiber density of the tubular liquid passage is higher than that of the subsection 17 and the capillary phenomenon occurring in this passage 16 is sufficient to ensure that urine quickly spreads in the longitudinal direction before any quantity of urine spreads from the passage 16.

Immediately after quick spread in the longitudinal direction under the capillary phenomenon occurring in the tubular liquid passage, urine spread also in the transverse direction through the subsections 17. In this way, a generally entire area of the core 2 can be utilized to absorb urine and a total quantity of urine discharged on the diaper 1C can be absorbed into the core 2 in a time as short as possible. In the case of this diaper 1C, sideway leakage of urine can be reliably prevented since there is no possibility that urine might immediately spread from the spot onto which urine has been discharged in the transverse direction. The movable zones 10b of the respective rising leak-barrier sheets 10 form the barriers against urine and thereby prevent any quantity of urine from leaking sideways beyond the side flaps 8.

Stock materials for the liquid-impervious second sheet 4 and the liquid-impervious leak-barrier sheets 10 may be selected from a hydrophobic fibrous nonwoven fabric, a breathable liquid-impervious plastic film, a composite nonwoven fabric comprising two or more layers of a hydrophobic fibrous nonwoven fabric laminated one upon another and a composite sheet comprising a hydrophobic fibrous nonwoven fabric and a breathable liquid-impervious plastic film laminated on each other. It is also possible to use a composite nonwoven fabric (SM nonwoven fabric or SMS nonwoven fabric) comprising a spun bond fibrous nonwoven fabric having a high strength and a high flexibility, placed on one surface of a melt blown fibrous nonwoven fabric having a high water-resistance as stock materials for the second sheet and the leak-barrier sheets 10.

The fibrous nonwoven fabric may be selected from those of spun lace-, needle punch-, melt blown-, thermal bond-, chemical bond and air through-types. The component fibers of the nonwoven fabric may be selected from polyolefin-based, polyester-based and polyamide-based fibers and core-and-sheath type or side-by-side type conjugate fibers of polyethylene/polypropylene or polyethylene/polyester.

Joining of the first and second sheets 3, 4 to each other, bonding of the leak-barrier sheets 10 to the sheets 3, 4 and securing of the elastic members 19, 20, 21 to the sheets 3, 4, 10 may be achieved by use of an adhesive or a welding technique such as a heat-sealing or sonic sealing technique.

The adhesive may be selected from a group consisting of hot melt adhesive, acrylic adhesive and rubber-based adhesive. The first and second sheets 3, 4 and the leak-barrier sheets 10 may be coated with the suitable adhesives in a spiral pattern, a zigzag pattern, a dotted pattern or striped pattern. These sheets are coated with the adhesive in such patterns to define an adhesive coated area and an area free from the adhesive.

These diapers 1A, 1B and 1C may be exploited also in a manner that the upper and lower sections 14, 15 defining the tubular liquid passage 16 have the same fiber density as the subsections 17, 18 of the upper and lower sections 14, 15 except the tubular liquid passage have. It is also possible to use two or more layers of hydrophilic fibrous nonwoven fabrics laminated one upon another to form the liquid-pervious first sheet 3.

The present invention is applicable not only to the open-type diaper 1A, 1B, 1C in which the front and rear waist regions are connected with each other when the diaper is put on the wearer, but also to the pants-type diaper in which the side flaps in the front and rear waist regions are previously connected with one another so as to form a waist-hole and a pair of leg-holes.

In the disposable diaper according to the present invention, the upper section of the first sheet extends upward, in the vicinity of the longitudinal center line, generally describing a loop and thereby defines the tubular liquid passage extending along the longitudinal center line. Urine discharged onto the diaper on the wearer first permeates through the tubular liquid passage contacting the wearer's urethral organs so as to spread in the longitudinal direction under a capillary effect of this passage, then vertically permeates downwardly through the tubular liquid passage so as to spread in the transverse direction through the subsection of the upper section except the tubular liquid passage. In this way, a generally entire area of the core can be utilized to absorb urine and total quantity of discharged urine can be absorbed by the core in a time as short as possible. With this diaper, it is not apprehended that discharged urine might immediately spread in the transverse direction from the spot on which urine has been discharged and any quantity of urine might leak sideways.

Also in the case of the embodiment in which the lower section of the first sheet extends from the upper surface of the core through the slit of the core and generally describes a loop bulging above the core and cooperates with the upper section to define the tubular liquid passage, the effect as has been described above is achieved. Specifically, after having spread in the longitudinal direction through the tubular liquid passage, urine permeates downward through the tubular liquid passage, thereafter permeates in the transverse direction through the subsection of the upper section except the tubular liquid passage as well as the subsection of the lower section except the tubular liquid passage. Consequently, urine is absorbed by the core not only through the upper surface but also the lower surface of the core and total quantity of discharged urine can be absorbed by the core in the further shorter time.

With the diaper in which the tubular liquid passage has a fiber density higher than that in the subsections of the upper and lower sections except the tubular liquid passage, the capillary phenomenon occurring in the tubular liquid passage 16 is sufficient to ensure that discharged urine quickly spreads in the longitudinal direction before discharged urine can move from the tubular liquid passage to the subsections of the upper and lower sections. Even after urine has moved from the tubular liquid passage to these subsections, spread of urine in the longitudinal direction is sufficiently promoted relative to spread of urine in the transverse direction to ensure that spread of urine in the longitudinal direction can progress before urine spreads in the transverse direction.

What is claimed is:

1. A disposable diaper having a front waist region, a rear waist region and a crotch region extending between said front and rear waist regions, said diaper comprising:
  a liquid-absorbent core having an upper surface facing a wearer's skin and a lower surface facing away from the wearer's skin and extending over said crotch region and further into said front and rear waist regions;
  a liquid-pervious first sheet having an upper section covering said upper surface of said core and a lower section covering said lower surface of said core; and
  a liquid-impervious second sheet lying outside said lower section of said first sheet;
  said upper section of said first sheet extending upwardly, in a vicinity of a longitudinal center line bisecting a transverse dimension of said diaper, from said upper surface of said core so as to define a tubular liquid passage extending in a longitudinal direction along said longitudinal center line; and
  said tubular liquid passage extending at least from said front waist region toward said crotch region.

2. The diaper according to claim 1 wherein:
  a slit formed completely through said core in a thickness direction thereof along said longitudinal center line extends in the longitudinal direction at least from said front waist region toward said crotch region; and
  said lower section of said first sheet extends upward from said lower surface of said core through said slit so as to be exposed above said slit, generally describing a loop and cooperates with said upper section to define said tubular liquid passage.

3. The diaper according to claim 1, wherein said first sheet is formed from a hydrophilic fibrous nonwoven fabric and said upper section defining said tubular liquid passage has a fiber density higher than a fiber density in a subsection of said upper section except said tubular liquid passage.

4. The diaper according to claim 2, wherein said lower section defining said tubular liquid passage has a fiber density higher than a fiber density in a subsection of said lower section except said tubular liquid passage.

5. The diaper according to claim 1, wherein the upper section of said first sheet describes a shape of Ω.

6. The diaper according to claim 2, wherein the lower section of said first sheet describes a shape of Ω.

7. The diaper according to claim 3, wherein the tubular liquid passage is configured to provide a capillary effect in the longitudinal direction, so that bodily liquid discharged on the tubular liquid passage spreads in the longitudinal direction before spreading in a transverse direction perpendicular to the longitudinal direction.

8. The diaper according to claim 1, wherein the tubular liquid passage extends, in said longitudinal direction, over an entire length of said absorbent core.

9. The diaper according to claim 2, wherein the slit and the tubular liquid passage extend, in said longitudinal direction, over an entire length of said absorbent core.

10. The diaper according to claim 2, wherein the lower section of said first sheet is joined to itself in the longitudinal direction to define said loop.

11. A disposable diaper having a front waist region, a rear waist region and a crotch region extending in a longitudinal direction of said diaper between said front and rear waist regions, said diaper comprising:
  a liquid-absorbent core having an upper surface facing a wearer's skin and a lower surface facing away from the wearer's skin, said core extending in the longitudinal direction from said front waist region to said rear waist region via said crotch region;

an upper liquid-pervious sheet section covering at least said upper surface of said core; and a lower liquid-impervious sheet disposed below said lower surface of said core;

said upper liquid-pervious sheet section comprising an upwardly convex portion which is located in a vicinity of a longitudinal center line bisecting a transverse dimension of said diaper and upwardly spaced from the upper surface of said core so as to define a passage between said upwardly convex portion and the upper surface of said core.

12. The diaper according to claim 11, further comprising a slit extending completely through an entire thickness of said core; and a lower liquid-pervious sheet section extending from below said lower surface of said core, upwardly, through said slit and defining another upwardly convex portion which is located above the upper surface of the core and below the upwardly convex portion of said upper liquid-pervious sheet section and defines together with said upwardly convex portion of said upper liquid-pervious sheet section a double wall of said passage.

13. The diaper according to claim 11, wherein said upper liquid-pervious sheet section further comprises transversely lateral portions respectively covering transversely lateral regions of the upper surface of said core and being continuous to and connected with each other by said upwardly convex portion, and a fiber density of said upper liquid-pervious sheet section in said upwardly convex portion is higher than in said transversely lateral portions so that said passage provides a capillary effect in the longitudinal direction, whereby bodily liquid discharged on the passage spreads in the longitudinal direction before spreading in a transverse direction perpendicular to the longitudinal direction.

14. The diaper according to claim 12, wherein said lower liquid-pervious sheet section further comprises transversely lateral portions respectively covering transversely lateral regions of the lower surface of said core, being positioned between the lower surface of said core and the liquid-impervious sheet, and being continuous to and connected with each other by said another upwardly convex portion, and a fiber density of said lower liquid-pervious sheet section in said another upwardly convex portion is higher than in said transversely lateral portions so that said passage provides a capillary effect in the longitudinal direction, whereby bodily liquid discharged on the passage spreads in the longitudinal direction before spreading in a transverse direction perpendicular to the longitudinal direction.

15. The diaper according to claim 13, wherein the upwardly convex portion and said transversely lateral portions of said upper liquid-pervious sheet section together describe a shape of $\Omega$.

16. The diaper according to claim 14, wherein said another upwardly convex portion and said transversely lateral portions of said lower liquid-pervious sheet section together describe a shape of $\Omega$.

17. The diaper according to claim 11, wherein the passage is tubular and extends longitudinally along said longitudinal center line at least from said front waist region toward said crotch region.

18. The diaper according to claim 11, wherein the passage extends, in said longitudinal direction, over an entire length of said absorbent core.

19. The diaper according to claim 12, wherein the slit and the tubular liquid passage extend, in said longitudinal direction, over an entire length of said absorbent core.

20. The diaper according to claim 12, wherein said another upwardly convex portion of said lower liquid-pervious sheet section is joined to itself in the longitudinal direction to define a tubular shape of said passage.

* * * * *